United States Patent [19]

Sacks

[11] Patent Number: 4,613,463

[45] Date of Patent: Sep. 23, 1986

[54] PROCESS AND INTERMEDIATES FOR THE PREPARATION OF 17 ALPHAHYDROXYPROGESTERONES AND CORTICOIDS FROM AN ENOL STEROID

[75] Inventor: Clifford E. Sacks, Portage, Mich.

[73] Assignee: The Upjohn Company, Kalamazoo, Mich.

[21] Appl. No.: 667,023

[22] Filed: Nov. 1, 1984

[51] Int. Cl.$^4$ ............................................. C07J 21/00
[52] U.S. Cl. ................................. 540/94; 260/397.45; 540/63; 540/64; 540/69; 540/70; 540/88; 540/89
[58] Field of Search ............................. 260/239.55 R

[56] References Cited

U.S. PATENT DOCUMENTS

| | | | |
|---|---|---|---|
| 3,822,114 | 7/1974 | Montgomery | 8/111 |
| 3,998,829 | 12/1976 | Phillips et al. | 260/239.55 R |
| 4,041,055 | 8/1977 | Shephard et al. | 260/397.3 |

OTHER PUBLICATIONS

DiFuria, F., et al., "Mechanism of Oxygen Transfer from Peroxo Species", Pure. & Appl. Chem., vol. 54, No. 10, pp. 1853–1866 (1982);

Montgomery, R. E., et al., "Catalyst of Peroxymonosulfate Reactions by Ketones", JACS, 96, 7820–7821 (1974);

Edwards, J. O., et al., "On the Formation and Reactivity of Dioxirane Intermediates in the Reaction of Peroxoanions with Organic Substrates*", Photochemistry and Photobiology, vol. 30, pp. 63–70 (1979);

Gallopo, A. R., et al., "Kinetics and Mechanism of the Oxidation of Pyridine by Caro's Acid Catalyzed by Ketones", J. Org. Chem. 46, pp. 1684–1688 (1981).

Curci, R., et al., "Epoxidation of Alkenes by Dioxirane Intermediates Generated in the Reaction of Potassium Caroate with Ketones", J. Org. Chem. 45, pp. 4758–4760 (1980);

Suryawanski S. N., et al., "Synthesis of Gamma-Hydroxy Enones via Persulfate Oxidation of Dienyl Ethers", Tetrahedron Letters, 22, pp. 4203–4204 (1981).

Mimoun H., "Oxygen Transfer from Inorganic and Organic Peroxides to Organic Substrates: A Common Mechanism?", Angew. Chem. Int. Ed. Engl., 21, pp. 734–750 (1982).

*Primary Examiner*—Elbert L. Roberts
*Attorney, Agent, or Firm*—William G. Jameson

[57] ABSTRACT

This invention discloses an improved process for the production of corticoids from 17α-hydroxy steroids utilizing peroxymonosulfate.

20 Claims, No Drawings

PROCESS AND INTERMEDIATES FOR THE PREPARATION OF 17 ALPHAHYDROXYPROGESTERONES AND CORTICOIDS FROM AN ENOL STEROID

BACKGROUND OF THE INVENTION

The conversion of 17α-hydroxy steroid (I) to produce a corticosteroid (II) by addition of a peracid is well known to those skilled in the art. See U.S. Pat. No. 4,041,055, Col. 6, lines 35–67 and Col. 14, line 59 to Col. 15, line 20 et al.

The general method of conversion is to react the 17α-hydroxy steroid with a peracid and the corresponding ester alcohol and/or of the peracid is obtained as a corticoid product. For example, if the peracid is peracetic acid the 21-acetate of the corticoid is produced as a mixture with the free alcohol. See Example 17, U.S. Pat. No. 4,041,055, et al. However, that procedure yields less of the corticoid product 11β,17α-dihydroxy-21-acetoxy-4,9(11)-pregnene-3,20-dione when 11β,17α-dihydroxy-20-phenoxy-pregna-4,9(11),20-trien-3-one is reacted with peracetic acid. The advantage of the process of the present invention is a surprising and unexpected increase in yield of product and the ability to isolate the 20,21 epoxide.

20,21-epoxy-20-alkyl-pregnanes are disclosed in U.S. Pat. No. 3,998,829. See Col. 9, lines 1–4.

F. DiFuria, et al. in *Pure & Appl. Chem.*, Vol. 54, No. 10, pp. 1853–1866 (1982) describe the mechanisms of the polar oxygen transfer from peroxo and metal peroxo species.

R. E. Montgomery in *JACS*, 96, 7820–21 (1974) reported that certain ketones catalyze a number of peroxymonosulfate ion ($HSO_5^-$) reactions in weakly alkaline solutions. See also U.S. Pat. No. 3,822,114.

J. O. Edwards, et al. in *Photochemistry and Photobiology*, Vol. 30, pp. 63–70 (1979) suggests the involvement of dioxirane intermediates in the ketone-catalyzed decomposition of peroxymonosulfate (Caroate) $HSO_5^-$. OXONE ® (Dupont de Nemours) is described as a mixture of potassium peroxomonosulfate (Caroate), $KHSO_4$ and $K_2SO_4$ containing approximately 42% of the peroxide and ca. 4.5% active oxygen.

A. R. Gallopo, et al. in *J. Org. Chem.*, 1981, 46, 1684–1688 reported the kinetics of the oxidation of pyridine by peroxomonosulfate ion catalyzed by acetone and cyclohexanone.

R. Curci, et al. in *J. Org. Chem.*, 1980, 45, 4758–4760 described the epoxidation of alkenes by dioxirane intermediates generated in the reaction of potassium caroate with ketones and also reports the use of a catalytic amounts of 18-crown-6 and tetrabutylammonium hydrogen sulfate as phase-transfer catalysts.

S. N. Suryawanski and P. L. Fuchs in *Tetrahedron Letters*, 22, 4201 (1981) reported that a dienol ether could be converted to a γ-hydroxy-α,β-unsaturated ketone by reaction with $KHSO_5$ in tetrahydrofuran, sodium bicarbonate and water.

H. Mimoun in *Angew. Chem. Int. Ed. Engl.*, 21, (1982) 734–750 describes various selective oxygen-transfer reactions from inorganic and organic peroxides to organic substrates; including the proposed mechanism of generation of dioxiranes in the reactions of most organic peroxides.

None of the above references describes the application of peroxidation reactions to the synthesis of corticosteroids.

SUMMARY OF THE INVENTION

Disclosed is a process for the preparation of a steroid (III) which comprises starting with a 17α-substituted steroid (I) and $C_3$ protected forms thereof and adding peroxymonosulfate in the presence of catalytic amounts of selected ketones and a phase transfer catalyst. The 20,21-epoxide (II) can be isolated, if desired, from the organic phase of the reaction mixture.

DETAILED DESCRIPTION OF THE INVENTION

The present invention discloses a process for the preparation of a steroid (III) from a 17α-substituted steroid (I) and the steps of the reaction are more fully disclosed in Chart A.

The 17α-substituted steroid (I) starting materials are well known to those skilled in the art or can be readily prepared from known compounds by methods well known to those skilled in the art. See, for example, U.S. Pat. No. 4,041,055.

The D-ring of the 17-substituted steroid (I) can be combined with various combinations of A, B and C rings (see CHART B for formulas A–C).

Considered as equivalent of the A-ring functionalities of IA and IB are the $C_3$ protected ketal forms as is well known to those in the art. The $C_3$ protected forms are readily interconvertible and interchangeable with the $C_3$ non-protected forms. For the $\Delta^4$-3-keto steroids (A) when the $C_3$ ketone is to be protected, it is protected as the ketal (Ab) as is well known in the art. The preferred ketal (Ab) is the ethylene ketal. The ketals are prepared by well known methods, see Steroid Reactions, edited by Carl Djerassi, Holden-Day, San Francisco 1963, page 42–45.

It is preferred that the A-B ring saturation/unsaturation be $\Delta^4$-3-keto (A) and $C_3$ protected forms thereof or $\Delta^{1,4}$-3-keto (B).

$R_3$ is alkyl of 1 thru 5 carbon atoms with the proviso that with the ketal (Ab), the $R_3$ groups can be the same or different and can be connected.

Various substitutions at $C_6$, $C_9$ and $C_{11}$ are well known to the art. $R_6$ can be in either the α or β configuration and is a hydrogen, methyl, chlorine, fluorine or bromine atom. $R_9$ is alpha and can be nothing or a hydrogen, chlorine, fluorine or a bromine or oxygen atom, which includes the $\Delta^{9(11)}$ when $R_9$ is nothing and 9β,11β-epoxide functionality when $R_9$ and $R_{11}$ taken together are an oxygen atom. $R_{11}$ is a hydrogen, hydroxy, chlorine, bromine, fluorine or oxygen atom, which includes $\Delta^{9(11)}$ when $R_{11}$ is a hydrogen atom and the 9β,11β-epoxide functionality when $R_9$ and $R_{11}$ taken together are an oxygen atom and ⋯⋯⋯⋯ between $C_{11}$ and $R_{11}$ is a single bond.

⋯⋯⋯⋯ is a single or double bond and ∼ indicates that the attached group can be in either the α or β configuration. X is a hydrogen atom or nothing.

In Formulas I, II and/or III, $R_{16}$ is either a hydroxyl or methyl group and may be in either the α or β configuration; $R_{17}$ is hydrogen or —COZ group, where Z is alkyl of one to four carbon atoms, phenyl or phenyl substituted with (alkyl of one thru four carbon atoms, or substituted with one thru three nitro groups, substituted with one thru three trifluoromethyl groups or substituted with one thru three halogen atoms); $R_{16}$ and $R_{17}$ can be taken together to form the acetonide; $R_{20}$ is alkyl of one thru 5 carbon atoms, phenyl or phenyl substituted with alkyl of one thru 4 carbon atoms or alkoxy of one thru 3 carbon atoms. Examples of alkyl of one thru 5 carbon atoms are methyl, ethyl, propyl, butyl, pentyl and isomeric forms thereof. Examples of phenyl substituted with alkyl of one thru 4 carbon atoms are (o-, m-, or p-)tolyl, (o-, m-, or p-)ethylphenyl, p-tertbutylphenyl, 2,5-dimethylphenyl, 2,6-dimethylphenyl, 2,4-dimethylphenyl, (2,3,4-, 2,3,5-, 2,3,6-, or 2,4,6- or 2,4,5-)-trimethylphenyl. Examples of phenyl substituted with alkoxy of one thru 3 carbon atoms are (o-, m-, or p-)methoxyphenyl, 2,4-dimethoxyphenyl, 2,5-dimethoxyphenyl, 2,6-dimethylphenyl, 2,4,6-trimethoxyphenyl or (o-, m-, or p-) ethoxyphenyl. It is preferred that $R_{20}$ is phenyl. $R_{21}$ is a hydrogen atom, alkyl carboxylate of 2 thru 6 carbon atoms, alkyl dicarboxylate of 2 thru 6 carbon atoms or aromatic carboxylate of 7 thru 12 carbon atoms. Examples of alkyl carboxylates of 2 thru 6 carbon atoms are acetyl, propionyl, butyryl, valeryl, hexanoyl, and isomers thereof. An example of alkyl dicarboxylate is hemisuccinate. Examples of aromatic carboxylate of 7 thru 12 carbom atoms are benzoyl, phenylacetyl, phenylpropionyl, phenylbutyryl, phenylvaleryl, phenylhexanoyl, and isomers thereof.

Peroxymonosulfate ($HSO_5^-$) is known, see R. E. Montgomery, J. Am. Chem. Soc., 96, 7820 (1974) and U.S. Pat. No. 3,822,114.

Peroxymonosulfate ($HSO_5^-$) can be added as potassium peroxomonosulfate (potassium caroate, $KHSO_5$), preferably as OXONE ® (DuPont de Nemours), a mixture of $2KHSO_5 \cdot KHSO_4 \cdot K_2SO_4$, or an equivalent preparation.

The reaction of a 17α-substituted steroid (I) and $C_3$-protected forms thereof with peroxymonosulfate is biphasic and is buffered and carried out in the presence of a ketone selected from the group consisting of acetone, methyl ethyl ketone, diethyl ketone, cyclohexanone and cyclopentanone, preferably acetone and suitable organic solvent(s). Suitable organic solvents are water-immiscible and nonhydrolytic and include: chloroform, carbon tetrachloride, methylene chloride, toluene, benzene, hexane, heptane or mixtures thereof, preferably methylene chloride. Suitable buffers include phosphate or carbonate. A phase transfer catalyst such as n-tetrabutylammonium bisulfate, 18-Crown-6, n-tetrabutylammonium chloride or bromide, polyethylene glycol ethers (including polyethelene glycol mono or dimethyl ethers mw 200–900, preferably 200–400), and polyethylene glycols, preferably n-tetrabutylammonium bisulfate or polyethylene glycols mw 200 to 900, preferably 200–400, are utilized.

The reaction is preferably carried out at about 40° C. but a temperature range of about 25° C. to about 100° C. can be utilized. A quantity of solvent sufficient to totally dissolve the starting 17α-hydroxy steroid is preferred. An amount of peroxymonosulfate sufficient to oxidize the 17α-substituted steroid, i.e. at least an equal molar amount, is placed in solution and added dropwise, with agitation, to the reaction mixture at about pH 7.0–9.0, preferably 8.2–8.5.

The reaction is monitored by thin-layer chromatography (TLC) and improved yields and purity are obtained if the reaction is run to just short of completion (about 98% complete).

The hot reaction mixture is filtered, phases separated, and the aqueous phase extracted with an appropriate organic solvent such as methylene chloride, chloroform, toluene, ethyl acetate or benzene. The organic phase is washed with dilute base such as sodium hydroxide, sodium carbonate or sodium bicarbonate; and the base phase back-extracted with the appropriate organic solvent. The combined organic phases are clarified (water removed) and the 20,21-epoxy steroid (II) recovered, if desired, or the organic solvent replaced with a solvent such as tetrahydrofuran and a mineral or sulfonic acid such as hydrochloric, hydrobromic, hydrochloric, sulfuric, fluoboric, p-toluenesulfonic or methylsulfonic added and the hydrolysis reaction carried out at 0° C., preferably 45° C. When the reaction is complete by TLC, the reaction mixture is worked-up according to procedures well known to those skilled in the art. Alternatively, an organic acid such as acetic acid or succinic acid may be substituted and the corresponding 21-ester is isolated.

DEFINITIONS

The definitions and explanations below are for the terms as used throughout the entire patent application including both the specification and claims.

All temperatures are in degrees Centigrade.

TLC refers to thin-layer chromatography.

THF refers to tetrahydrofuran.

Saline refers to an aqueous saturated sodium chloride solution.

NMR refers to nuclear (proton) magnetic resonance spectroscopy, chemical shifts are reported in ppm ($\delta$) downfield from TMS.

TMS refers to tetramethylsilane.

When solvent pairs are used, the ratio of solvents used are volume/volume (v/v).

Fluoboric acid refers to $HBF_4$.

OXONE ® refers to DuPont de Nemours brand of a mixture of $2KHSO_5 \cdot KHSO_4 \cdot K_2SO_4$.

18-Crown-6 refers to $C_{12}O_6H_{24}$, a cyclic polyether.

avmw refers to average molecular weight.

EXAMPLES

Without further elaboration, it is believed that one skilled in the art can, using the preceeding description, practice the present invention to its fullest extent. The following detailed examples describe how to prepare the various compounds and/or perform the process of the invention and are to be construed as merely illustrative, and not limitations of the preceeding disclosure in any way whatsoever. Those skilled in the art will promptly recognize appropriate variations from the procedures both as to reactants as well as to reaction conditions and techniques.

EXAMPLE 1

11β,17α-dihydroxy-21-acetoxypregna-4-ene-3,20-dione

A potassium phosphate buffer is prepared by adding 3.4 ml of 85% phosphoric acid to 500 ml water adjusting to pH 8.0 with 30% potassium hydroxide and diluting to 1 liter. 11β,17-dihydroxy-20-phenoxypregna-4,20-diene-3-one (5.00 grams, 0.0118 mole) is slurried in the pH 8 potassium phosphate buffer (40 ml, 0.05M in $PO_4^\equiv$). Acetone (20 ml, 0.272 mole), polyethylene glycol average molecular weight 300 (0.72 grams, 0.0024 mole) and methylene chloride (50 ml) are added to give a two phase reaction. 10.0 grams, 0.0163 moles of OXONE ® ($2KHSO_5 \cdot KHSO_4 \cdot K_2SO_4$; supplied by Aldrich Chemical) is dissolved in water (30 ml), filtered and placed in an additional funnel. The reaction mixture is heated to 35° C. and stirred at 600 rpm with a paddle stirrer or mechanical or magnetically coupled stirring device while the OXONE solution is added dropwise while maintaining a constant pH of 8.3 to 8.7 with 30% potassium hydroxide. The reaction is run to about 98% completion as indicated by TLC. The hot reaction mixture is pressure filtered thru a coarse fritted funnel to remove inorganics. The organic layer (lower layer) is separated and washed with two portions of 30 ml of 5% sodium hydroxide and clarified thru solka flok filter aid to remove water and any dissolved salts. Methylene chloride is replaced with 25 ml tetrahydrofuran (THF) and water (2.0 ml, 0.11 mole) is added followed by 50% fluoboric acid (0.05 ml, 0.00038 mole). The solution is stirred at 25° C. and near the end of the hydrolysis a heavy precipitate forms (hydrocortisone). THF (100 ml) is added and then the slurry is distilled to a final volume of 100 ml to azeotropically remove water. Acetic anhydride (2.8 ml, 0.030 mole), triethylamine (0.2 ml, 0.0015 mole) and dimethylaminopiperidine (0.050 grams, 0.00024 mole) are added and the slurry stirred at 40° C. until acetylation is complete (ca. 3 hrs). THF is removed on a rotoevaporator. To the residue is added methylene chloride (15 ml) and water (15 ml). The product is collected by filtration, rinsed with water and dried in a 70° C. vacuum oven. 3.64 grams of crystalline 11$\beta$,17-dihydroxy-21-acetoxyprega-4-ene-3,20-dione is obtained.

EXAMPLE 2

11$\beta$,17$\alpha$-dihydroxy-21-acetoxypregna-1,4-diene-3,20-dione

A potassium phosphate buffer is prepared by diluting 6 ml of 85% phosphoric acid to 400 ml and adding 30% (w/w) potassium hydroxide to adjust to pH 8 and diluting to final volume of 500 ml with water.

Part A: 37.75 ml of methylene chloride, 14.5 ml of acetone, 27.75 ml of pH 8 phosphate buffer and polyethylene glycol average molecular weight 300 (0.42 grams, 1.4 mmole) are combined and 11$\beta$,17$\alpha$-dihydroxy-20-phenoxypregna-1,4,20-trien-3-one (3.0 grams, 7.13 mmole) added and the mixture stirred at 35° C. An excess of OXONE ® sufficient to oxidize the starting material, is dissolved in 63 ml of water and filtered thru a medium frit filter and added dropwise at 35° C. while maintaining a constant pH of 8.2 to 8.5 throughout the addition by adding 30% potassium hydroxide. When completed, the reaction mixture is filtered thru a 'C' frit with nitrogen. The water layer is extracted with methylene chloride. The combined organics are washed with 100 ml of 1% sodium hydroxide solution and filtered thru a solka flok filter and concentrated on a rotary evaporator to give 3.65 grams of 11$\beta$,17$\alpha$-dihydroxy-20,21-epoxy-20-phenoxy-pregna-1,4-diene-3-one.

Part B: 15 ml of tetrahydrofuran (THF), 0.375 ml of water and 0.12 ml of 50% (7.6N) fluoboric acid is added to the 11$\beta$,17$\alpha$-dihydroxy-20,21-epoxy-20-phenoxy-pregna-1,4-diene-3-one to hydrolyze it to give 11$\beta$,17$\alpha$,21-trihydroxypregna-1,4-diene-3,20-dione over about 1 hour.

Part C: 15 ml of THF is added and the volume reduced to 15 ml on a rotary evaporator to remove the water. 1.59 grams (2.2 ml), 2.2 mmole of triethylamine (TEA, d=0.726), 1.56 grams (1.5 ml), 15.7 mmole of acetic anhydride and 8.3 mg of 4-dimethylaminopyridine (DMAP) is added and stirred at 40° C. for 1½ hours. The reaction mixture is cooled to room temperature (22° C.) and reduced to a thick slurry on a rotary evaporator, then added slowly to a mixture of 300 ml of water and 38 ml of n-hexane being vigorously stirred. The solid is filtered and washed with hexane, dried at 70° C. in a vacuum oven for about 12–16 hours to give 2.05 grams of prednisolone-21-acetate.

EXAMPLE 3

17$\alpha$-hydroxy-21-acetoxypregna-4,9(11)-diene-3,20-dione

17$\alpha$-hydroxy-20-phenoxy-pregna-4,9(11), 20-trien-3-one (20.0 grams, 49.5 mmoles) is slurried in a mixture of pH 8 potassium phosphate buffer (100 ml, 0.1M $PO_4\equiv$) and water (100 ml). Acetone (20 ml) methylene chloride (200 ml) and polyethylene glycol (3.0 g avg. MW=300) are added and the two phase mixture heated to 35° C. and adjusted to pH 8.5 with potassium hydroxide. OXONE ® ($2KHSO_5 \cdot KHSO_4 \cdot K_2SO_4$), 30 g, 48.8 mmoles) is dissolved in water (110 ml) containing (10 ml of a 5% by weight solution of sodium edetate) and the ($Na_4EDTA$) solution added dropwise over 1 hour with vigorous agitation while maintaining the pH at 8.3 to 8.5 When the reaction is complete, the phases are separated hot and the aqueous phase extracted twice with 50 ml of methylene chloride. The combined organics are washed twice with 100 ml of aqueous 5% sodium hydroxide and clarified thru through solka flok (10 g). The solvent is removed by distillation and replaced with tetrahydrofuran to a final volume of 150 ml. Water (3 ml) containing fluoboric acid (0.3 ml of 50%) is added to hydrolyze the epoxide at 45–50° C. After 1 hour, acetic anhydride (30 ml, 318 mmoles), triethylamine (0.35 ml, 2.63 mmoles) and N,N-dimethylaminopyridine (0.1 g, 0.47 mmoles) are added at 55° C. to acetylate the 21-alcohol. When complete, tetrahydrofuran is replaced with acetone by atmospheric distillation to a final volume of 100 ml. 17$\alpha$-hydroxy-21-acetoxypregna-4,9(11)-diene-3,20-dione was isolated by filtration and drying under vacuum at 60° to yield 16.7 g.

EXAMPLE 4

17$\alpha$-hydroxy-20,21-epoxy-20-phenoxypregna-4,9(11)-diene-3-one

17$\alpha$-hydroxy-20-phenoxypregna-4,9(11),20-trien-3-one (4.04 grams, 10 mmoles) is slurried in pH 8 potassium phosphate buffer (50 ml, 0.02M $PO_457$ ), 40 ml methylene chloride, 0.222 grams (1 mmole), of Ansul ether 181 ($C_{10}H_{22}O_5$) and 20 ml acetone and the two phase mixture heated to 25° C. and adjusted to pH 8.5 with 30% potassium hydroxide. 18.4 grams, 30 mmoles of OXONE ® ($2KHSO_5 \cdot KHSO_4 \cdot K_2SO_4$) is dissolved in 90 ml of water and 10 ml of a 5% by weight solution of $Na_4EDTA$ and the resulting solution added dropwise at 25° C. with vigorous agitation while maintaining the pH at 8.0–8.5 with 30% potassium hydroxide. When the reaction is complete the phases are separated hot and the aqueous phase extracted twice with 50 ml of methylene chloride. The combined organics are washed twice with 100 ml of aqueous 5% sodium hydroxide and clarified thru a solka flok filter and concentrated on a rotary evaporator to yield 17$\alpha$-hydroxy-20,21-epoxy-20-phenoxypregna-4,9(11)-diene-3-one.

NMR ($CDCl_3$): 0.89, 1.04, 1.4, 2.60, 2.86, 5.50, 5.67, 6.9–7.2.

EXAMPLE 5

11β,17α-dihydroxy-21-acetoxypregna-1,4-diene-3,20-dione and

11β,17α,21-trihydroxypregna-1,4-diene-3,20-dione

11β,17α-dihydroxy-20-phenoxypregna-1,4,20-triene-3-one (4.2 grams, 9.99 mmole) is slurried in a pH 8 potassium phosphate buffer (34 ml, 0.05M in $PO_4\equiv$). Acetone (17 ml), polyethylene glycol average molecular weight 300 (0.61 grams, 2.03 mmol) and methylene chloride (42 ml) are added to give a two-phase reaction mixture. OXONE ® (16.8 gms, 27.3 m) is dissolved in water (50 ml), filtered thru a medium frit filter, and placed in an addition funnel. The reaction mixture is heated to 40° C. and stirred vigorously while 46 ml of the OXONE solution is added dropwise at pH 8.2–8.8 by addition of 30% potassium hydroxide using a pH stat. The hot reaction mixture is suction-filtered thru a coarse frit filter to remove inorganics. The inorganics are washed with two 10 ml portions of methylene chloride (2×10 ml). The combined organic layer is separated and the aqueous layer back-extracted with two 20 ml portions of methylene chloride (2×20 ml). The combined methylene chloride phases are washed with two 25 ml portions of a 5% sodium hydroxide solution (2×25 ml) and the sodium hydroxide phase back-extracted with three 10 ml portions of methylene chloride (3×10 ml). The combined methylene chloride phases are clarified thru a solka flok filter and the methylene chloride removed on a rotary evaporator and replaced with 21 ml of tetrahydrofuran (THF), water (1.7 ml) and 0.04 ml, 0.305 mmol of 50% (7.6 N) aqueous fluoboric acid. The mixture is stirred for 1½ hours at 22° C. THF (84 ml) is added and the mixture concentrated to 84 ml to remove water and mixture divided in half and identified A & B (2×42 ml) and worked up as follows in Part I & II to yield prednisolone and prednisolone 21-acetate, the title compounds.

Part I 42 ml of the above solution (Part A) is mixed with 0.1 ml (0.07 g, 0.7 mmole) triethylamine and concentrated to a residue which is dissolved in 15 ml methylene chloride, and 15 ml of water and 15 ml of n-heptane added. The product is filtered and redissolved in a minimum amount of methanol and methylene chloride and treated with 1.2 grams Darco brand decolorizing carbon. The residue is filtered and concentrated to a residue on a rotary evaporator. 15 ml methylene chloride is added and the mixture heated on a steam bath, 15 ml n-heptane is added and then the mixture is cooled. The solids are collected by filtration and dried at 70° C. in vacuum oven for 12–16 hours to yield 1.10 grams of 11β,17α,21-trihydroxy-pregna-1,4-diene-3,20-dione.

Part II 1.3 grams (1.2 ml), 12.7 mmol of acetic anhydride, 0.14 grams (0.2 ml), 1.4 mmol of triethylamine (TEA, d=0.726), and 0.022 grams (0.18 mmole) of 4-dimethylaminopyridine (DMAP) are added to 42 ml of the above solution (Part B) and the mixture is stirred forD 12–16 hours at ambient temperature. THF is removed on a rotavapor and 7.5 ml of methylene chloride are added to the residue along with 7.5 ml of water and 7.5 ml of n-heptane. The product is collected by filtration and the solid is washed with 7.5 ml of water and 7.5 ml of n-heptane; dried in a vacuum oven at 70° C. for 12–16 hours to give 1.65 grams of 11β,17α-dihydroxy-21-acetoxypregna-1,4-diene-3,20-dione. The filtrates contain product also but are contaminated by other components.

EXAMPLE 6

11β,17α-dihydroxy-21-acetoxypregna-1,4-diene-3,20-dione

11β,17α-dihydroxy-20-phenoxypregna-1,4,20-triene-3-one (4.2 grams, 9.99 mmole) is slurried in a pH 8 potassium phosphate buffer (34 ml, 0.05M in $PO_4\equiv$). Acetone (17 ml, 231 mmole), polyethylene glycol, avmw 300 (0.61 grams, 2.03 mmol) and methylene chloride (42 ml) are added to give a two phase reaction mixture. OXONE ® (17.0 grams, 27.6 mmol) is dissolved in 50.8 ml of water, filtered thru a medium frit, and placed in an addition funnel. The reaction mixture is stirred and heated at 40° C. while 34 ml of the OXONE solution is added dropwise at pH 8.3–8.7 by addition of a 30% potassium hydroxide solution using a pH stat. The hot reaction mixture is suction filtered thru a 'C' frit: phases separated, and the aqueous phase extracted with three 20 ml portions of methylene chloride (inorganics are washed with 20 ml methylene chloride). The methylene chloride layer is washed with two 20 ml portions of 5% sodium hydroxide solution. The sodium hydroxide phase is back-extracted with two 20 ml portions of methylene chloride. The combined methylene chloride phases are filtered thru solka flok and stripped to dryness on a rotary evaporator (~5.2 grams). Methylene chloride is replaced by 21 ml of tetrahydrofuran (THF) and 1.7 ml water and 0.04 ml, 0.305 mmol of 50% (7.6N) aqueous fluoboric acid are added. The mixture is stirred at ambient tempeature for 1½ hours. THF (84 ml) is added and the solution concentrated by 84 ml on a rotary evaporator to remove water.

2.6 grams (2.4 ml), 25.4 mmol of acetic anhydride, 0.14 grams (0.2 ml), 1.4 mmol of triethylamine (TEA, d=0.726), and 0.042 grams (0.34 mmol) of 4-dimethylaminopyridine (DMAP) are added and the mixture stirred for 12–16 hours at ambient temperature. THF is removed on a rotavapor and 15 ml methylene chloride is added to the residue along with 15 ml of water and 15 of ml n-heptane. The product is collected by filtration and the solid washed with 15 ml water and 15 ml n-heptane, and dried in a vacuum oven at 70° C. for 12–16 hours to give 2.75 grams of 11β,17α-dihydroxy-21-acetoxypregna-1,4-diene-3,20-dione.

EXAMPLE 7

11β,17α-dihydroxy-21-acetoxypregna-1,4-diene-3,20-dione

11β,17α-dihydroxy-20-phenoxypregna-1,4,20-triene-3-one (4.2 grams, 9.99 mmole) is slurried in a pH 8 potassium phosphate buffer (34 ml, 0.05M in $PO_457$ ). Acetone (17 ml, 231 mmole), polyethylene glycol, avmw 300 (0.61 grams, 2.03 mmol) and methylene chloride (42 ml) are added to give a two phase reaction mixture. OXONE ® (17.0 grams, 27.6 mmol) is dissolved in 50.8 ml of water, filtered thru a medium frit, and placed in an addition funnel. The reaction mixture is stirred and heated at 40° C. while 34 ml of the OXONE solution is added dropwise at pH 8.2–8.8 (maintained by addition of a 30% potassium hydroxide solution using a pH stat). The hot reaction mixture is suction filtered thru a 'C' frit: phases are separated, and the aqueous phase extracted with three 20 ml portions of methylene chloride (inorganics are washed with 20 ml methylene chloride). The methylene chloride layer is washed with two 20 ml portions of 5% sodium hydroxide solution. The sodium hydroxide phase is back-extracted with two 20 ml portions of methylene chloride. The combined methylene chloride phase is filtered thru solka flok and stripped to dryness on a rotary evaporator (~5.2 grams). Methylene chloride is replaced by 21 ml of tetrahydrofuran (THF) and 1.7 ml water and 0.04 ml, 0.305 mmol of 50% (7.6N) aqueous fluoboric acid added. The mixture is stirred at ambient temperature for 1½ hours. THF (84 ml) added and the solution concentrated to 84 ml on a rotary evaporator to remove water.

2.6 grams (2.4 ml), 25.4 mmol of acetic anhydride, 0.14 grams (0.2 ml), 1.4 mmol of triethylamine (TEA, d=0.726), and 0.042 grams (0.34 mmol) of 4-dimethylaminopyridine (DMAP) is added and the mixture stirred for 12–16 hours at ambient temperature. THF is removed on a rotavapor and 15 ml methylene chloride are added to the residue along with 15 ml of water and 15 ml of n-heptane. The product is collected by filtration and the solid washed with 15 ml of water and 15 ml of n-heptane, and dried in a vacuum oven at 70° C. for 12–16 hours to give 2.9 grams of 11$\beta$,17$\alpha$-dihydroxy-21-acetoxypregna-1,4-diene-3,20-dione.

EXAMPLE 8

11$\beta$,17$\alpha$21-trihydroxypregna-4-ene-3,20-dione

11$\beta$,17$\alpha$-hydroxy-20-phenoxypregna-4,20-diene-3-one (1.00 gram, 2.37 mmole) is dissolved in 20 ml of toluene and 5 ml of methylene chloride, and slurried in 10 ml of pH 8 potassium phosphate buffer (prepared as in Example 1) containing 0.17 gm (0.5 mmole) of n-tetrabutylammonium bisulfate and 2 ml of acetone. The epoxidation reaction is conducted at 10° and a solution of 3.6 gm (5.8 mmole) of OXONE ® in 20 ml H$_2$O are added dropwise, with stirring, and the pH maintained, by pH stat, between 7.6 and 8.3 with 15% sodium hydroxide. The reaction mixture is stirred for 10 additional minutes; no starting material could be detected (TLC) in an NaHSO$_3$/HCl—quenched aliquot. Six ml of 1M NaHSO$_3$ is then added, the pH adjusted to 2.5 with sulfuric acid, and the reaction mixture allowed to warm to room temperature, with stirring. The organic layer is separated and 2 ml of acetic acid added. After washing with NaHCO$_3$, the organic layer is concentrated and hydrocortisone is isolated.

EXAMPLE 9

17$\alpha$-hydroxy-21-acetoxypregna-4,9(11)-diene-3,20-dione

17$\alpha$-hydroxy-20-phenoxypregna-4,9(11),20-trien-3-one (4.05 grams, 10 mmoles) is slurried with 210 ml of an aqueous pH 8 potassium phosphate buffer (0.5M in PO$_4^\equiv$), 20 ml of acetone, 40 ml of toluene/methylene chloride (3:2) and n-tetrabutylammonium bromide is (0.645 grams, 2.0 mmoles) added. The pH is adjusted to 7.0 to 8.0 and the mixture cooled to 15° C. and an OXONE ® solution is (18.4 gms, 30 mmoles dissolved in 65 ml of water) added dropwise by an addition funnel while stirring and maintaining pH at 7.0 to 8.0 by addition of a 30% potassium hydroxide solution. The reaction is worked up by separating the layers and replacing the organic solvent with toluene to a volume of 100 ml so as to remove water. After cooling to 10° C., 3 ml of glacial acetic acid is added. The product is isolated by replacing the toluene with acetone and filtering to obtain 3.12 g of 17$\alpha$-hydroxy-21-acetoxypregna-4,9(11)-diene-3,20-dione.

Following the same general procedures of this example but using toluene in place of the toluene/methylene chloride mixture and using n-tetrabutylammonium bisulfate (0.645 grams, 2.0 mmoles) in place of the n-tetrabutylammonium bromide, 2.98 grams of 17$\alpha$-hydroxy-21-acetoxypregna-4,9(11)-diene-3,20-dione is obtained.

EXAMPLE 10

17$\alpha$-hydroxy-21-acetoxypregna-4,9(11)-diene-3,20-dione

17$\alpha$-hydroxy-20-phenoxypregna-4,9(11),20-trien-3-one (4.05 grams, 10 mmoles) is slurried in a 250 ml round bottom flask, in an aqueous pH 8 potassium phosphate buffer (20 ml, 0.05M in PO$_4^\equiv$) prepared as in Example 1. Tetra n-butylammonium bromide (0.64 grams, 2.0 mmole), acetone (20 ml), methylene chloride (40 ml) are added and the mixture cooled to 15° C. 18.42 grams, 30 mmoles of OXONE ® (2KHSO$_5$.KHSO$_4$.K$_2$SO$_4$) is dissolved in 62 ml of water filtered and placed in an addition funnel. The OXONE solution is added dropwise with stirring while maintaining the pH between 6.8 and 7.2 with 30% potassium hydroxide. The reaction is run to completion. Fifty ml of water is added and the reaction mixture is filtered. The filtered solids are rinsed with methylene chloride and water, the layers are separated and the methylene chloride layer is filtered thru a solka flok filter. Two ml of glacial acetic acid are added and the mixture is stirred for 1 hour to yield 2.5 grams of 17$\alpha$-hydroxy-21 -acetoxy-pregna-4,9(11)-diene-3,20-dione at room temperature.

EXAMPLE 11

Following the procedure of Example 2, Part A, and Example 4 but substituting the following 17$\alpha$-hydroxy steroids:

17$\alpha$-hydroxy-20-phenoxypregna-1,4,9(11),20-tetraen-3-one;

11$\beta$-17$\alpha$-dihydroxy-20-phenoxypregna-4,20-diene-3-one;

17$\alpha$-hydroxy-16$\beta$-methyl-20-phenoxypregna-4,9(11),20-trien-3-one; 17$\alpha$-hydroxy-16$\beta$-methyl-20-phenoxypregna-1,4,9(11),20-trien-3-one;

17$\alpha$-hydroxy-20-phenoxypregna-4,20-diene-3-one;

17$\alpha$-hydroxy-20-phenoxypregna-1,4,20-trien-3-one;

17$\alpha$-hydroxy-16$\alpha$-methyl-20-phenoxypregna-4,9(11),20-trien-3-one;

17$\alpha$-hydroxy-6$\alpha$-methyl-20-phenoxypregna-4,9(11),20-trien-3-one;

11$\beta$,17$\alpha$-dihydroxy-16$\beta$-methyl-20-phenoxypregna-1,4,20-trien-3-one;

11$\beta$,17$\alpha$-dihydroxy-16$\alpha$-methyl-20-phenoxypregna-4,20-diene-3-one;

17$\alpha$-hydroxy-6$\alpha$-methyl-20-phenoxypregna-1,4,9(11),20-tetraen-3-one;

11$\beta$,17$\alpha$-dihydroxy-6$\alpha$-methyl-20-phenoxypregna-4,20-diene-3-one;

11$\beta$,17$\alpha$-dihydroxy-6$\alpha$-methyl-20-phenoxypregna-1,4,20-trien-3-one;

11$\beta$,17$\alpha$-dihydroxy-6$\alpha$-fluoro-20-phenoxypregna-4,20-diene-3-one;

11$\beta$,17$\alpha$-dihydroxy-6-$\alpha$-fluoro-20-phenoxypregna-1,4,20-trien-3-one;

17$\alpha$-hydroxy-6$\alpha$-fluoro-20-phenoxypregna-1,4,9(11),20-tetraen-3-one;

11β,17α-dihydroxy-16α-methyl-20phenoxypregna-1,4,20-trien-3-one;
17α-hydroxy-16α-methyl-20-phenoxypregna-1,4,20-trien-3-one;
11β,17a-dihydroxy-9α-chloro-16β-methyl-20-phenoxypregna-1,4,20-trien-3-one;
11β,17α-dihydroxy-9α-fluoro-16β-methyl-20-phenoxypregna-1,4,20-trien-3-one;
17α-hydroxy-20-phenoxypregna-4,20-diene-3,11-dione;
11β,17α-dihydroxy-9α-fluoro-16α-methyl-20-phenoxypregna-1,4,20-trien-3-one;
11β,17α-dihydroxy-6α,9α-difluoro-16β-methyl-20-phenoxypregna-1,4,20-trien-3-one;
11β,17α-dihydroxy-9α-fluoro-20-phenoxypregna-4,20-diene-3-one;
11β,17α-dihydroxy-6α,9α-difluoro-16α-methyl-20-phenoxypregna-1,4,20-trien-3-one;
11β,17α-dihydroxy-6α-fluoro-16α-methyl-20-phenoxypregna-1,4,20-trien-3-one;
17α-hydroxy-20-phenoxypregna-1,4,20-triene-3,11-dione;
for the 11β,17α-dihydroxy-20-phenoxypregna-1,4,20-trien-3-one of Example 2 or the 17α-hydroxy-20-phenoxypregna-4,9(11),20-trien-3-one of Example 4 there are obtained the corresponding 20,21-epoxides:
17α-hydroxy-20,21-epoxy-20-phenoxypregna-1,4,9(11)-trien-3-one;
11β,17α-dihydroxy-20,21-epoxy-20-phenoxypregna-4-en-3-one;
17α-hydroxy-16β-methyl-20,21-epoxy-20-phenoxypregna-4,9(11)-diene-3-one;
17α-hydroxy-16β-methyl-20,21-epoxy-20-phenoxypregna-1,4,9(11)-trien-3-one;
17α-hydroxy-20,21-epoxy-20-phenoxypregna-4-en-3-one;
17α-hydroxy-20,21-epoxy-20-phenoxypregna-1,4-diene-3-one;
17α-hydroxy-16α-methyl-20,21-epoxy-20-phenoxypregna-4,9(11)-diene-3-one;
17α-hydroxy-6α-methyl-20,21-epoxy-20-phenoxypregna-4,9(11)-diene-3-one;
11β,17α-dihydroxy-16α-methyl-20,21-epoxy-20-phenoxypregna-1,4-diene-3-one;
11β,17α-dihydroxy-16β-methyl-20,21-epoxy-20-phenoxypregna-1,4-en-3-one;
17α-hydroxy-6α-methyl-20,21-epoxy-20-phenoxypregna-1,4,9(11)-trien-3-one;
11β,17α-dihydroxy-6α-methyl-20,21-epoxy-20-phenoxypregna-4-en-3-one;
11β,17α-dihydroxy-6α-methyl-20,21-epoxy-20-phenoxypregna-1,4-diene-3-one;
11β,17α-dihydroxy-6α-fluoro-20,21-epoxy-20-phenoxypregna-4-en-3-one;
11β,17α-dihydroxy-6α-fluoro-20,21-epoxy-20-phenoxypregna-1,4-diene-3-one;
17α-hydroxy-6α-fluoro-20,21-epoxy-20-phenoxypregna-1,4,9(11)-trien-3-one;
11β,17α-dihydroxy-16α-methyl-20,21-epoxy-20-phenoxypregna-1,4-diene-3-one;
17α-hydroxy-16α-methyl-20,21-epoxy-20-phenoxypregna-1,4-diene-3-one;
11β,17α-dihydroxy-9α-chloro-16β-methyl-20,21-epoxy-20-phenoxypregna-1,4-diene-3-one;
11β,17α-dihydroxy-9α-fluoro-16β-methyl-20,21-epoxy-20-phenoxypregna-1,4-diene-3-one;
17α-hydroxy-20,21-epoxy-20-phenoxypregna-4-ene-3,11-dione;
11β,17α-dihydroxy-9α-fluoro-16α-methyl-20,21-epoxy-20-phenoxypregna-1,4-diene-3-one;
11β,17α-dihydroxy-6α,9α-difluoro-16β-methyl-20,21-epoxy-20-phenoxypregna-1,4-diene-3-one;
11β,17α-dihydroxy-9α-fluoro-20,21-epoxy-20-phenoxypregna-4-en-3-one;
11β,17α-dihydroxy-6α,9α-difluoro-16α-methyl-20,21-epoxy-20-phenoxypregna-1,4-diene-3-one;
11β,17α-dihydroxy-6α-fluoro-16α-methyl-20,21-epoxy-20-phenoxypregna-1,4-diene-3-one;
17α-hydroxy-20,21-epoxy-20-phenoxypregna-1,4-diene-3,11-dione.

EXAMPLE 12

Following the procedure of Example 2, Part I, Parts A and B or Example 5, part I, but substituting the following 17α-hydroxy steroids in Part A:
17α-hydroxy-20-phenoxypregna-4,9(11),20-trien-3-one;
17α-hydroxy-20-phenoxypregna-1,4,9(11),20-tetraene-3-one;
11β,17α-dihydroxy-20-phenoxypregna-4,20-diene-3-one;
17α-hydroxy-16β-methyl-20-phenoxypregna-4,9(11),20-trien-3-one;
17α-hydroxy-16β-methyl-20-phenoxypregna-1,4,9(11),20-trien-3-one;
17α-hydroxy-20-phenoxypregna-4,20-diene-3-one;
17α-hydroxy-20-phenoxypregna-1,4,20-trien-3-one;
17α-hydroxy-16α-methyl-20-phenoxypregna-4,9(11),20-trien-3-one;
17α-hydroxy-6α-methyl-20-phenoxypregna-4,9(11),20-trien-3-one;
11β, 17α-dihydroxy-16β-methyl-20-phenoxypregna-1,4,20-trien-3-one;
11β,17α-dihydroxy-16α-methyl-20-phenoxypregna-4,20-diene-3-one;
17α-hydroxy-6α-methyl-20-phenoxypregna-1,4,9(11),20-tetraen-3-one;
11β,17α-dihydroxy-6α-methyl-20-phenoxypregna-4,20-diene-3-one;
11β,17α-dihydroxy-6α-methyl-20-phenoxypregna-1,4,20-trien-3-one;
11β,17α-dihydroxy-6α-fluoro-20-phenoxypregna-4,20-diene-3-one;
11β,17α-dihydroxy-6α-fluoro-20-phenoxypregna-1,4,20-trien-3-one;
17α-hydroxy-6α-fluoro-20-phenoxypregna-1,4,9(11),20-tetraen-3-one;
11β,17α-dihydroxy-16α-methyl-20-phenoxypregna-1,4,20-trien-3-one;
17α-hydroxy-16α-methyl-20-phenoxypregna-1,4,20-trien-3-one;
11β,17a-dihydroxy-9α-chloro-26β-methyl-20-phenoxypregna-1,4,20-trien-3-one;
11β,17α-dihydroxy-9α-fluoro-16β-methyl-20-phenoxypregna-1,4,20-trien-3-one;
17α-hydroxy-20-phenoxypregna-4,20-diene-3,11-dione;
11β,17α-dihydroxy-9α-fluoro-16α-methyl-20-phenoxypregna-1,4,20-trien-3-one;
11β,17α-dihydroxy-6α,9α-difluoro-16β-methyl-20-phenoxypregna-1,4,20-trien-3-one;
11β,17α-dihydroxy-9α-fluoro-20-phenoxypregna-4,20-diene-3-one;
11β,17α-dihydroxy-6α,9α-difluoro-16α-methyl-20-phenoxypregna-1,4,20-trien-3-one;
11β,17α-dihydroxy-6α-fluoro-16α-methyl-20-phenoxypregna-1,4,20-trien-3-one;

17α-hydroxy-20-phenoxypregna-1,4,20-triene-3,11-dione;

for 11β,17α-dihydroxy-20-phenoxypregna-1,4,20-trien-3-one there are obtained the corresponding steroids:
17α,21-dihydroxy-pregna-4,9(11)-diene-3,20-dione;
17α,21-dihydroxy-pregna-1,4,9(11)-trien-3,20-dione,
11β,17α-21-trihydroxy-pregna-4-en-3,20-dione;
17α,21-dihydroxy-16β-methylpregna-4,9(11)-diene-3,20-dione;
17α,21-dihydroxy-16β-methylpregna-1,4,9(11)-trien-3,20-dione;
17α,21-dihydroxy-pregna-4-en-3,20-dione;
17α,21-dihydroxy-pregna-1,4-diene-3,20-dione;
17α,21-dihydroxy-16α-methylpregna-4,9(11)-diene-3,20-dione;
17α,21-dihydroxy-6α-methylpregna-4,9(11)-diene-3,20-dione;
11β,17α-trihydroxy-16α-methylpregna-1,4-diene-3,20-dione;
11β,17α,21-trihydroxy-16β-methylpregna-4-ene-3,20-dione;
17a,21-dihydroxy-6α-methylpregna-1,4,9(11)-triene-3,20-dione;
11β,17α,21-trihydroxy-6α-methylpregna-4-ene-3,20-dione;
11β,17α,21-trihydroxy-6α-methylpregna-1,4-dione-3,20-dione;
11β,17α,21-trihydroxy-6α-fluoropregna-4-ene-3,20-dione;
11β,17α,21-trihydroxy-6α-fluoropregna-1,4-diene-3,20-dione;
17α,21-dihydroxy-6α-fluoropregna-1,4,9(11)-triene-3,20-dione;
11β,17α,21-trihydroxy-16α-methylpregna-1,4-diene-3,20-dione;
17α,21-dihydroxy-16α-methylpregna-1,4-diene-3,20-dione;
11β,17α,21-trihydroxy-9α-chloro-16β-methylpregna-1,4-diene-3,20-dione;
11β,17α,21-trihydroxy-9α-fluoro-16β-methylpregna-1,4-diene-3,20-dione;
17α,21-dihydroxypregna-4-ene-3,11,20-trione;
11β,17α,21-trihydroxy-9α-fluoro-16α-methylpregna-1,4-diene-3,20-dione;
11β,17α,21-trihydroxy-6α,9α-difluoro-16β-methylpregna-1,4-diene-3,20-dione;
11β,17α21-trihydroxy-9α-fluoropregna-1,4-ene-3,20-dione;
11β,17α,21-trihydroxy-6α,9α-difluoro-16α-methylpregna-1,4-diene-3,20-dione;
11β,17α,21-trihydroxy-6α-fluoro-16α-methylpregna-1,4-diene-3,20-dione;
17α,21-dihydroxypregna-1,4-diene-3,11,20-trione.

EXAMPLE 13

Following the procedure of Example 3, but substituting the following 17α-hydroxy steroids:
17α-hydroxy-20-phenoxypregna-1,4,9(11),20-tetraen-3-one;
11β,17α-dihydroxy-20-phenoxypregna-4,20-diene-3-one;
17α-hydroxy-16β-methyl-20-phenoxypregna-4,9(11),20-trien-3-one;
17α-hydroxy-16β-methyl-20-phenoxypregna-1,4,9(11),20-trien-3-one;
17α-hydroxy-20-phenoxypregna-4,20-diene-3-one;
17α-hydroxy-20-phenoxypregna-1,4,20-trien-3-one;
17α-hydroxy-16α-methyl-20-phenoxypregna-4,9(11),20-trien-3-one;
17α-hydroxy-6α-methyl-20-phenoxypregna-4,9(11),20-trien-3-one;
11β,17α-dihydroxy-16β-methyl-20-phenoxypregna-1,4,20-trien-3-one;
11β,17α-dihydroxy-16α-methyl-20-phenoxypregna-4,20-diene-3-one;
17α-hydroxy-6α-methyl-20-phenoxypregna-1,4,9(11),20-tetraen-3-one;
11β,17α-dihydroxy-6α-methyl-20-phenoxypregna-4,20-diene-3-one;
11β,17α-dihydroxy-6α-methyl-20-phenoxypregna-1,4,20-trien-3-one;
11β,17α-dihydroxy-6α-fluoro-20-phenoxypregna-4,20-diene-3-one;
11β,17α-dihydroxy-6α-fluoro-20-phenoxypregna-1,4,20-trien-3-one;
17α-hydroxy-6α-fluoro-20-phenoxypregna-1,4,9(11),20-tetraen-3-one;
11β,17α-dihydroxy-16α-methyl-20-phenoxypregna-1,4,20-trien-3-one;
17α-hydroxy-16α-methyl-20-phenoxypregna-1,4,20-trien-3-one;
11β,17a-dihydroxy-9α-chloro-26β-methyl-20-phenoxypregna-1,4,20-trien-3-one;
11β,17α-dihydroxy-9α-fluoro-16β-methyl-20-phenoxypregna-1,4,20-trien-3-one;
17α-hydroxy-20-phenoxypregna-4,20-diene-3,11-dione;
11β,17α-dihydroxy-9α-fluoro-16α-methyl-20phenoxypregna-1,4,20-trien-3-one;
11β,17α-dihydroxy-6α,9α-difluoro-16β-methyl-20-phenoxypregna-1,4,20-trien-3-one;
11β,17α-dihydroxy-9α-fluoro-20-phenoxypregna-4,20-diene-3-one;
11β,17α-dihydroxy-6α,9α-difluoro-16α-methyl-20-phenoxypregna-1,4,20-trien-3-one;
11β,17α-dihydroxy-6α-fluoro-16α-methyl-20-phenoxypregna-1,4,20-trien-3-one;
17α-hydroxy-20-phenoxypregna-1,4,20-triene-3,11-dione;

for 17α-dihydroxy-20-phenoxypregna-4,9(11),20-trien-3-one there are obtained the corresponding 21-acetoxy steroids:
17α-hydroxy-21-acetoxypregna-1,4,9(11)-trien-3,20-dione;
11β,17α-dihydroxy-21-acetoxypregna-4-en-3,20-dione;
17α-hydroxy-16β-methyl-21-acetoxypregna-4,9(11)-diene-3-20-dione;
17α-hydroxy-16β-methyl-21-acetoxypregna-1,4,9(11)-trien-3,20-dione;
17α-hydroxy-21-acetoxypregna-4-en-3,20-dione;
17α-hydroxy-21-acetoxypregna-1,4-diene-3,20-dione;
17α-hydroxy-16α-methyl-21-acetoxypregna-4,9(11)-diene-3,20-dione;
17α-hydroxy-6α-methyl-21-acetoxypregna-4,9(11)-diene-3,20-dione;
11β,17α-dihydroxy-16α-methyl-21-acetoxypregna-1,4-diene-3,20-dione;
11β,17α-dihydroxy-16β-methyl-21-acetoxypregna-1,4-en-3,20-dione; 17α-hydroxy-6α-methyl-21-acetoxypregna-1,4,9(11)-trien-3,20-dione;
11β,17α-dihydroxy-6α-methyl-21-acetoxypregna-4-en-3,20-dione; 11β,17α-dihydroxy-6α-methyl-21-acetoxypregna-1,4-diene-3,20-dione;
11β,17α-dihydroxy-6α-fluoro-21-acetoxypregna-4-en-3,20-dione; 11β,17α-dihydroxy-6α-fluoro-21-acetoxypregna-1,4-diene-3,20-dione;

17α-hydroxy-6α-fluoro-21-acetoxypregna-1,4,9(11)-trien-3,20-dione;
11β,17α-dihydroxy-16α-methyl-21-acetoxypregna-1,4-diene-3,20-dione;
17α-hydroxy-16α-methyl-21-acetoxy-1,4-diene-3,20-dione;
11β,17α-dihydroxy-9α-chloro-16β-methyl-21-acetoxypregna-1,4-diene-3,20-dione;
11β,17α-dihydroxy-9α-fluoro-16β-methyl-21-acetoxypregna-1,4-dione-3,20-dione;
17α-hydroxy-21-acetoxypregna-4-ene-3,11,20-trione;
11β,17α-dihydroxy-9α-fluoro-16β-methyl-21-acetoxypregna-1,4-diene-3,20-dione;
11β-hydroxy-6α,9α-difluoro-16β-methyl-17,21-diacetoxypregna-1,4-diene-3,20-dione;
11β,17α-dihydroxy-9α-fluoro-21-acetoxypregna-4-ene-3,20-dione;
11β,17α-dihydroxy-6α,9α-difluoro-16α-methyl-21-acetoxypregna-1,4-diene-3,20-dione;
11β,17α-dihydroxy-6α-fluoro-16α-methyl-21-acetoxypregna-1,4-diene-3,20-dione;
17α-hydroxy-21-acetoxypregna-1,4-diene-3,11,20-trione.

CHART I

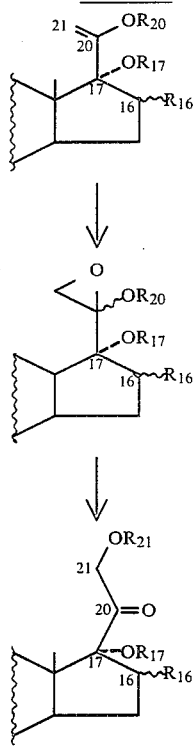

CHART B

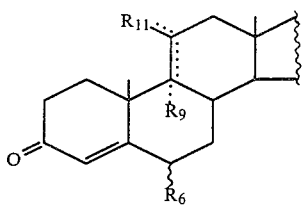
(A)

-continued
CHART B

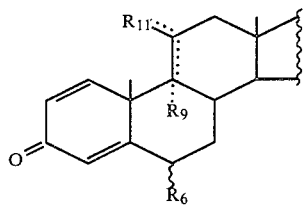
(B)

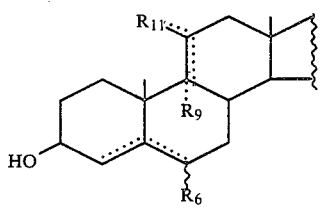
(C)

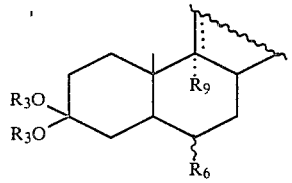
(Ab)

I claim:
1. A process for the preparation of a 17-substituted steroid of the formula:

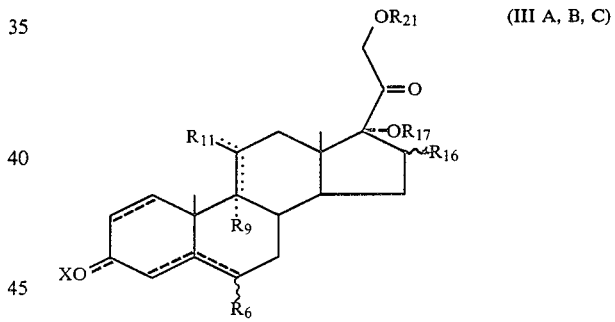
(III A, B, C)

and $C_3$ protected forms thereof, where X is a hydrogen atom or nothing, when X is nothing, the ------- at $C_3$ is a double bond, when X is a hydrogen atom the ------- at $C_3$ is a single bond; $R_6$ is a hydrogen, chlorine, fluorine or bromine atom, or methyl group; $R_9$ is nothing, a hydrogen, chlorine, fluorine, bromine or oxygen atom which makes the C-ring
  (a) $\Delta^{9(11)}$ when $R_9$ is nothing
  (b) 9β,11β-epoxide when $R_9$ and $R_{11}$ taken together are oxygen atom;
$R_{11}$ is a hydrogen, chlorine, bromine, fluorine or oxygen atom, two hydrogen atoms or α- or β-hydroxyl group which makes the C-ring
  (a) $\Delta^{9(11)}$ when $R_{11}$ is a hydrogen atom,
  (b) 9β,11β-epoxide when $R_9$ and $R_{11}$ taken together are oxygen atom and ------- between $C_{11}$ and $R_{11}$ is a single bond;
$R_{16}$ is either a hydrogen atom, a hydroxyl or methyl group; $R_{17}$ either a hydrogen or $$\overset{O}{\underset{\|}{-C}}Z$$

group where Z is alkyl of 1 to 4 carbon atoms, phenyl, or phenyl substituted with alkyl of one thru four carbon atoms, or substituted with one thru three nitro groups, substituted with one thru three trifluoromethyl groups or substituted with one thru three halogen atoms, with the proviso that $R_{16}$ and $R_{17}$ can be taken together to form the acetonide;

$R_{21}$ a hydrogen atom, alkyl carboxylate of 2 thru 6 carbon atoms, alkyl dicarboxylate of 2 thru 6 carbon atoms or aromatic carboxylate of 7 thru 12 carbon atoms;

........ is a single or double bond; ~ indicates that the attached atom or group can be in either the α or β configuration; and the ----- indicates the attached group is in the α configuration;

which comprises (1) contacting a 17α-substituted steroid of the formula (or a $C_3$ protected form thereof)

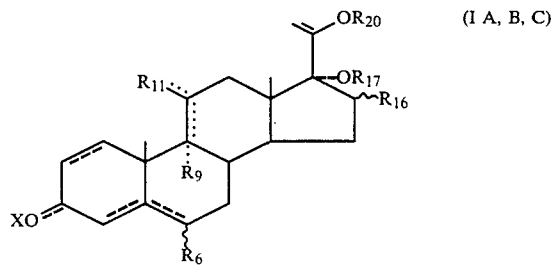

(I A, B, C)

where X, $R_6$, $R_9$, $R_{11}$, $R_{16}$, $R_{17}$, ........ , ~, ---- are defined above and $R_{20}$ is alkyl one thru 5 carbon atoms, phenyl or phenyl substituted with one alkyl of thru 4 carbon atoms or alkoxy of one thru 3 carbon atoms; with a peroxymonosulfate ion, in a biphasic reaction medium that is phase transfer catalyzed and contains a ketone;

(2) and reacting the product of step 1 with an acid.

2. A process according to claim 1 where the 17-substituted steroid (I) is selected from the group consisting of

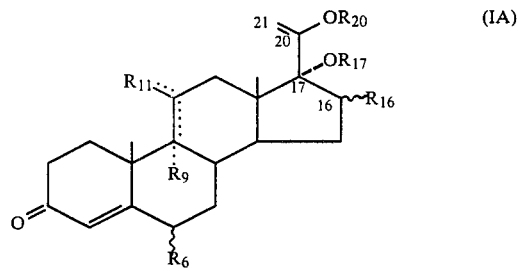

(IA)

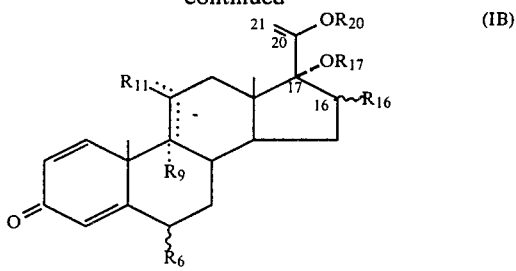

(IB)

and $C_3$ protected forms thereof.

3. A process according to claim 1 where the peroxymonosulfate ion is added as potassium peroxymonosulfate.

4. A process according to claim 1 where $R_{20}$ is phenyl.

5. A process according to claim 1 where the biphasic reaction medium is water and a solvent selected from the group consisting of methylene chloride, carbon tetrachloride, chloroform, toluene, benzene, hexane, heptane or mixtures thereof.

6. A process according to claim 1 where the acid is selected from the group consisting of fluoboric, hydrochloric, hydrobromic, hydroiodic, sulfuric, acetic, succinic, p-toluenesulfonic or methylsulfonic acid.

7. A process according to claim 1 where the phase transfer catalyst is is selected from the group consisting of n-tetrabutylammonium bisulfate, polyethylene glycol ethers mw 200–400, polyethylene glycols mw 200–400 and tetrabutylammonium bromide, or 18-Crown-6.

8. A process according to claim 1 where the biphasic reaction medium is water and a solvent selected from the group consisting of methylene chloride, carbon tetrachloride, chloroform, toluene, benzene, hexane, heptane or mixtures thereof; the acid is selected from the group consisting of fluoboric, hydrochloric, hydrobromic, hydroiodic, sulfuric, acetic, succinic, p-toluenesulfonic or methylsulfonic acid; the phase transfer catalyst is selected from the group consisting of n-tetrabutylammonium bisulfate, polyethylene glycol dimethyl ethers mw 200–400, polyethylene glycols mw 200–400 and tetrabutylammonium bromide; and the ketone is selected from the group consisting of acetone, methylethyl ketone or cyclohexanone.

9. A process according to claim 8 when the biphasic reaction medium is water and a solvent selected from the group consisting of methylene chloride, toluene or mixtures thereof; the acid is fluoboric, acetic or succinic; the phase transfer catalyst is n-tetrabutylammonium bisulfate or a polyethylene glycol mw 200 to 400; and the ketone is acetone or methylethyl ketone.

10. A process according to claim 2 where the steroid (III) is selected from the group consisting of:
11β,17α,21-trihydroxypregna-1,4-diene-3,20-dione;
17α,21-dihydroxy-pregna-4,9(11)-diene-3,20-dione;
17α,21-dihydroxy-pregna-1,4,9(11)-trien-3,20-dione,
11β,17α-21-trihydroxy-pregna-4-en-3,20-dione;
17α,21-dihydroxy-16β-methylpregna-4,9(11)-diene-3,20-dione;
17α,21-dihydroxy-16β-methylpregna-1,4,9(11)-trien-3,20-dione;
17α,21-dihydroxy-pregna-4-en-3,20-dione;
17α,21-dihydroxy-pregna-1,4-diene-3,20-dione;
17α,21-dihydroxy-16α-methylpregna-4,9(11)-diene-3,20-dione;

17α,21-dihydroxy-6α-methylpregna-4,9(11)-diene-3,20-dione;
11β,17α-trihydroxy-16α-methylpregna-1,4-diene-3,20-dione;
11β,17α,21-trihydroxy-16β-methylpregna-4-ene-3,20-dione;
17a,21-dihydroxy-6α-methylpregna-1,4,9(11)-triene-3,20-dione;
11β,17α,21-trihydroxy-6α-methylpregna-4-ene-3,20-dione;
11β,17α,21-trihydroxy-6α-methylpregna-1,4-dione-3,20-dione;
11β,17α,21-trihydroxy-6α-fluoropregna-4-ene-3,20-dione;
11β,17α,21-trihydroxy-6α-fluoropregna-1,4-diene-3,20-dione;
17α,21-dihydroxy-6α-fluoropregna-1,4,9(11)-triene-3,20-dione;
11β,17α,21-trihydroxy-16α-methylpregna-1,4-diene-3,20-dione;
17α,21-dihydroxy-16α-methylpregna-1,4-diene-3,20-dione;
11β, 17α,21-trihydroxy-9α-chloro-16β-methylpregna-1,4-diene-3,20-dione;
11β,17α,21-trihydroxy-9α-fluoro-16β-methylpregna-1,4-diene-3,20-dione;
17α,21-dihydroxypregna-4-ene-3,11,20-trione;
11β,17α,21-trihydroxy-9α-fluoro-16α-methylpregna-1,4-diene-3,20-dione;
11β,17α,21-trihydroxy-6α,9α-difluoro-16β-methyl-pregna-1,4-diene-3,20-dione;
11β,17α,21-trihydroxy-9α-fluoropregna-1,4-ene-3,20-dione;
11β,17α,21-trihydroxy-6α,9α-difluoro-16α-methyl-pregna-1,4-diene-3,20-dione;
11β,17α,21-trihydroxy-6α-fluoro-16α-methylpregna-1,4-diene-3,20-dione;
17α,21-dihydroxypregna-1,4-diene-3,11,20-trione.

11. A process according to claim 2 where the acid is acetic acid.

12. A process according to claim 11 where the steroid (III) is selected from the group consisting of:
17α-hydroxy-21-acetoxypregna-1,4,9(11)-trien-3,20-dione;
11β,17α-dihydroxy-21-acetoxypregna-4-en-3,20-dione;
17α-hydroxy-16β-methyl-21-acetoxypregna-4,9(11)-diene-3,20-dione;
17α-hydroxy-16β-methyl-21-acetoxypregna-1,4,9(11)-trien-3,20-dione;
17α-hydroxy-21-acetoxypregna-4-en-3,20-dione;
17α-hydroxy-21-acetoxypregna-1,4-diene-3,20-dione;
17α-hydroxy-16α-methyl-21-acetoxypregna-4,9(11)-diene-3,20-dione;
17α-hydroxy-6α-methyl-21-acetoxypregna-4,9(11)-diene-3,20-dione;
11β,17α-dihydroxy-16α-methyl-21-acetoxypregna-1,4-diene-3,20-dione;
11β,17α-dihydroxy-16β-methyl-21-acetoxypregna-1,4-en-3,20-dione;
17α-hydroxy-6α-methyl-21-acetoxypregna-1,4,9(11)-trien-3,20-dione;
11β,17α-dihydroxy-6α-methyl-21-acetoxypregna-4-en-3,20-dione;
11β,17α-dihydroxy-6α-methyl-21-acetoxypregna-1,4-diene-3,20-dione;
11β,17α-dihydroxy-6α-fluoro-21-acetoxypregna-4-en-3,20-dione;
11β,17α-dihydroxy-6α-fluoro-21-acetoxypregna-1,4-diene-3,20-dione;
17α-hydroxy-6α-fluoro-21-acetoxypregna-1,4,9(11)-trien-3,20-dione;
11β,17α-dihydroxy-16α-methyl-21-acetoxypregna-1,4-diene-3,20-dione;
17α-hydroxy-16α-methyl-21-acetoxy-1,4-diene-3,20-dione;
11β,17α-dihydroxy-9α-chloro-16β-methyl-21-acetoxypregna-1,4-diene-3,20-dione;
11β,17α-dihydroxy-9α-fluoro-16β-methyl-21-acetoxypregna-1,4-diene-3,20-dione;
17α-hydroxy-21-acetoxypregna-4-ene-3,11,20-trione;
11β,17α-dihydroxy-9α-fluoro-16β-methyl-21-acetoxypregna-1,4-diene-3,20-dione;
11β-hydroxy-6α,9α-difluoro-16β-methyl-17,21-diacetoxypregna-1,4-diene-3,20-dione;
11β,17α-dihydroxy-9α-fluoro-21-acetoxypregna-4-ene-3,20-dione;
11β,17α-dihydroxy-6α,9α-difluoro-16α-methyl-21-acetoxypregna-1,4-diene-3,20-dione;
11β,17α-dihydroxy-6α-fluoro-16α-methyl-21-acetoxypregna-1,4-diene-3,20-dione;
17α-hydroxy-21-acetoxypregna-1,4-diene-3,11,20-trione.

13. A process for the preparation of a 17α-substituted-20,21-epoxide of the formula

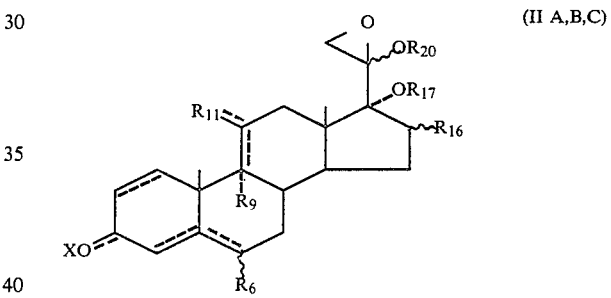

(II A,B,C)

and $C_3$ protected forms thereof, were X is nothing, the ......... at $C_3$ is a double bond, when X is a hydrogen atom the ......... at $C_3$ is a single bond; $R_6$ is a hydrogen, chlorine, fluorine or bromine atom, or methyl group; $R_9$ is nothing, a hydrogen, chlorine, fluorine, bromine or oxygen atom which makes the C-ring
  (a) $\Delta^{9(11)}$ when $R_9$ is nothing
  (b) 9β,11β-epoxide when $R_9$ and $R_{11}$ taken together are oxygen atom;
$R_{11}$ is a hydrogen, chlorine, bromine, fluorine or oxygen atom, two hydrogen atoms or α or β-hydroxyl group which makes the C-ring
  (a) $\Delta^{9(11)}$ when $R_{11}$ is a hydrogen atom,
  (b) 9β,11β-expoxide when $R_9$ and $R_{11}$ taken together are oxygen atom and ......... between $C_{11}$ and $R_{11}$ is a single bond;
$R_{16}$ is either a hydrogen atom, a hydroxyl or methyl group; $R_{17}$ either a hydrogen or

group where Z is alkyl of 1 to 4 carbon atoms, phenyl, or phenyl substituted with alkyl of one thru four carbon atoms, or substituted with one thru three nitro groups, substituted with one thru three trifluoromethyl groups or substituted with one thru three halogen atoms; with the proviso that $R_{16}$ and $R_{17}$ can be taken together to form the acetonide;

$R_{20}$ is alkyl of one thru 5 carbon atoms, phenyl or phenyl substituted with alkyl of one thru 4 carbon atoms or alkoxy of one thru 3 carbon atoms; which comprises contacting a 17α-substituted steroid of the formula

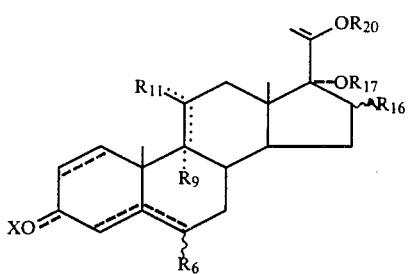

(I A, B, C)

or $C_3$ protected forms thereof, where X, $R_6$, $R_9$, $R_{11}$, $R_{16}$, $R_{17}$, $R_{20}$, ⋯⋯ , ~, ----- are defined above, with a peroxymonosulfate ion, in a biphasic reaction medium that is phase transfer catalyzed and contains a ketone.

14. A process according to claim 13, where $R_{20}$ is phenyl.

15. A process according to claim 13 where the biphasic reaction medium is water and a solvent selected from the group consisting of methylene chloride, carbon tetrachloride, chloroform, toluene, benzene, hexane, heptane or mixtures thereof; the phase transfer catalyst is selected from the group consisting of n-tetrabutylammonium bisulfate, polyethylene glycol dimethyl ethers mw 200–400, 18-Crown-6, polyethylene glycols mw 200–400 and tetrabutylammonium bromide; and the ketone is selected from the group consisting of acetone, methylethyl ketone or cyclohexanone.

16. A process according to claim 15 where the biphasic reaction medium is water and a solvent selected from the group consisting of methylene chloride, toluene or mixtures thereof; the phase transfer catalyst is n-tetrabutylammonium bisulfate or a polyethylene glycol mw 200 to 400; and the ketone is acetone or methylethyl ketone.

17. A process according to claim 13 where the $R_{20}$ is phenyl.

18. A process according to claim 13 where the 17α-substituted-20,21-epoxide (II) is selected from the group consisting of 11β,17α-dihydroxy-20,21-epoxy-20-phenoxypregna-1,4,20-trien-3-one;
17α-hydroxy-20,21-epoxy-20-phenoxypregna-4,9(11)-diene-3-one;
17α-hydroxy-20,21-epoxy-20-phenoxypregna-1,4,9(11)-trien-3-one;
11β,17α-dihydroxy-20,21-epoxy-20-phenoxypregna-4-en-3-one;
17α-hydroxy-16β-methyl-20,21-epoxy-20-phenoxypregna-4,9(11)-diene-3-one;
17α-hydroxy-16β-methyl-20,21-epoxy-20-phenoxypregna-1,4,9(11)-trien-3-one;
17α-hydroxy-20,21-epoxy-20-phenoxypregna-4-en-3-one;
17α-hydroxy-20,21-epoxy-20-phenoxypregna-1,4-diene-3-one;
17α-hydroxy-16α-methyl-20,21-epoxy-20-phenoxypregna-4,9(11)-diene-3-one;
17α-hydroxy-6α-methyl-20,21-epoxy-20-phenoxypregna-4,9(11)-diene-3-one;
11β,17α-dihydroxy-16α-methyl-20,21-epoxy-20-phenoxypregna-1,4-diene-3-one;
11β,17α-dihydroxy-16β-methyl-20,21-epoxy-20-phenoxypregna-1,4-en-3-one;
17α-hydroxy-6α-methyl-20,21-epoxy-20-phenoxypregna-1,4,9(11)-trien-3-one;
11β,17α-dihydroxy-6α-methyl-20,21-epoxy-20-phenoxypregna-4-en-3-one;
11β,17α-dihydroxy-6α-methyl-20,21-epoxy-20-phenoxypregna-1,4-diene-3one;
11β,17α-dihydroxy-6α-fluoro-20,21-epoxy-20-phenoxypregna-4-en-3-one;
11β,17α-dihydroxy-6α-fluoro-20,21-epoxy-20-phenoxypregna-1,4-diene-3-one;
17-hydroxy-6α-fluoro-20,21-epoxy-20-phenoxypregna-1,4,9(11)-trien-3one;
11β,17α-dihydroxy-16α-methyl20,21-epoxy-20-phenoxypregna-1,4-diene-3-one;
17α-hydroxy-16α-methyl-20,21-epoxy-20-phenoxypregna-1,4-diene-3-one;
11β,17α-dihydroxy-9α-chloro-16β-methyl-20,21-epoxy-20-phenoxypregna-1,4-diene-3-one;
11β,17α-dihydroxy-9α-fluoro-16β-methyl-20,21-epoxy-20phenoxypregna-1,4-diene-3-one;
17α-hydroxy-20,21-epoxy-20phenoxypregna-4-ene-3,11-dione;
11β,17α-dihydroxy-9α-fluoro-16α-methyl-20,21-epoxy-20-phenoxypregna-1,4-diene-3-one;
11β,17α-dihydroxy-6α,9α-difluoro-16β-methyl-20,21-epoxy-20-phenoxypregna-1,4-diene-3-one;
11β,17α-dihydroxy-9α-fluoro-20,21-epoxy-20-phenoxypregna-4-en-3-one;
11β,17α-dihydroxy-6α,9α-difluoro-16α-methyl-20,21-epoxy-20-phenoxypregna-1,4-diene-3-one;
11β,17α-dihydroxy-6α-fluoro-16α-methyl-20,21-epoxy-20-phenoxypregna-1,4-diene-3-one;
17α-hydroxy-20,21-epoxy-20-phenoxypregna-1,4-diene-3,11-dione.

19. A 17α-substituted 20,21-epoxide of the formula

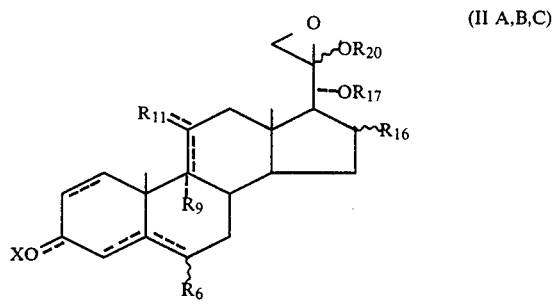

(II A,B,C)

and $C_3$ protected forms thereof, where X is nothing, the ⋯⋯ at $C_3$ is a double bond, when X is a hydrogen atom the ⋯⋯ at $C_3$ is a single bond; $R_6$ is a hydrogen, chlorine, fluorine or bromine atom, or methyl group; $R_9$ is nothing, a hydrogen, chlorine, fluorine, bromine or oxygen atom which makes the C-ring (a) $\Delta^{9(11)}$ when $R_9$ is nothing (b) 9β,11β-epoxide when $R_9$ and $R_{11}$ taken together are oxygen atom;

$R_{11}$ is a hydrogen, chlorine, bromine, fluorine or oxygen atom, two hydrogen atoms or α- or β-hydroxyl group which makes the C-ring (a) $\Delta^{9(11)}$ when $R_{11}$ is a hydrogen atom, $9\beta,11\beta$-epoxide when $R_9$ and $R_{11}$ taken together are oxygen atom and between $C_{11}$ and $R_{11}$ is a single bond;

$R_{16}$ is either a hydrogen atom, a hydroxyl or methyl group; $R_{17}$ either a hydrogen or

group where Z is alkyl of 1 to 4 carbon atoms, phenyl, or phenyl substituted with alkyl of one thru four carbon atoms, or substituted with one thru three nitro groups, substituted with one thru three trifluoromethyl groups or substituted with one thru three halogen atoms; with the proviso that $R_{16}$ and $R_{17}$ can be taken together to form the acetonide;

$R_{20}$ is phenyl or phenyl substituted with alkyl of one thru 4 carbon atoms or alkoxy of one thru 3 carbon atoms.

20. A compound according to claim 19 selected from the group consisting of:

17α-hydroxy-20,21-epoxy-20-phenoxypregna-4,9(11)-diene-3-one;
17α-hydroxy-20,21-epoxy-20-phenoxypregna-1,4,9(11)-trien-3-one;
11β,17α-dihydroxy-20,21-epoxy-20-phenoxypregna-4-en-3-one;
17α-hydroxy-16β-methyl-20,21-epoxy-20-phenoxypregna-4,9(11)-diene-3-one;
17α-hydroxy-16β-methyl-20,21-epoxy-20-phenoxypregna-1,4,9(11)-trien-3-one;
17α-hydroxy-20,21-epoxy-20-phenoxypregna-4-en-3-one;
17α-hydroxy-20,21-epoxy-20-phenoxypregna-1,4-diene-3-one;
17α-hydroxy-16α-methyl-20,21-epoxy-20-phenoxypregna-4,9(11)-diene-3-one;
17α-hydroxy-6α-methyl-20,21-epoxy-20-phenoxyprenga-4,9(11)-diene-3-one;
11β,17α-dihydroxy-16α-methyl-20,21-epoxy-20-phenoxypregna-1,4-diene-3-one;
11β,17α-dihydroxy-16β-methyl-20,21-epoxy-20-phenoxypregna-1,4-en-3-one;
17α-hydroxy-6α-methyl-20,21-epoxy-20-phenoxypregna-1,4,9(11)-trien-3-one;
11β,17α-dihydroxy-6α-methyl-20,21-epoxy-20-phenoxypregna-4-en-3-one;
11β,17α-dihydroxy-6α-methyl-20,21-epoxy-20-phenoxypregna-1,4-diene-3-one;
11β,17α-dihydroxy-6α-fluoro-20,21-epoxy-20-phenoxypregna-4en-3-one;
11β,17α-dihydroxy-6α-fluoro-20,21-epoxy-20-phenoxypregna-1,4-diene-3-one;
17-hydroxy-6α-fluoro-20,21-epoxy-20-phenoxypregna-1,4,9(11)-trien-3-one;
11β, 17α-dihydroxy-16α-methyl-20,21-epoxy-20-phenoxypregna-1,4-diene-3-one;
17α-hydroxy-16α-methyl-20,21-epoxy-20-phenoxypregna-1,4-diene-3-one;
11β,17α-dihydroxy-9α-chloro-16β-methyl-20,21-epoxy20-phenoxypregna-1,4-diene-3-one;
11β, 17α-dihydroxy-9α-fluoro-16β-methyl-20,21-epoxy-20-phenoxypregna-1,4-diene-3one;
17α-hydroxy-20,21-epoxy-20-phenoxypregna-4-ene-3,11-dione;
11β,17α-dihydroxy-9α-fluoro-16α-methyl-20,21-epoxy-20-phenoxypregna-1,4-diene-3-one;
11β,17α-dihydroxy-6α,9α-difluoro-16β-methyl-20,21-epoxy-20-phenoxypregna-1,4-diene-3-one;
11β,17α-dihydroxy-9α-fluoro-20,21-epoxy-20-phenoxypregna-4-en-3-one;
11β, 17α-dihydroxy-6α,9α-difluoro-16α-methyl-20,21-epoxy-20-phenoxypregna-1,4-diene-3-one;
11β, 17α-dihydroxy-6α-fluoro-16α-methyl-20,21-epoxy-20-phenoxypregna-1,4-diene-3-one;
17α-hydroxy-20,21-epoxy-20-phenoxypregna-1,4-diene-3,11-dione.

* * * * *